United States Patent [19]

Andrews

[11] Patent Number: 5,486,540
[45] Date of Patent: Jan. 23, 1996

[54] CYCLOPENTANE HEPTANOIC OR HEPTENOIC ACID, 2-ARYLALKYL OR ARYLALKENYL AND DERIVATIVES AS THERAPEUTIC AGENTS

[75] Inventor: Steven W. Andrews, Irvine, Calif.

[73] Assignee: Allergan, Inc., Irvine, Calif.

[21] Appl. No.: 144,968

[22] Filed: Oct. 28, 1993

[51] Int. Cl.[6] .................. A61K 31/215; A61K 31/19; A61K 31/045
[52] U.S. Cl. .................. 514/530; 514/573; 514/724; 514/913
[58] Field of Search .................. 514/530, 573, 514/724, 913

[56] References Cited

U.S. PATENT DOCUMENTS

| 4,494,274 | 2/1991 | Chan et al. . |
| 4,599,353 | 7/1991 | Bito . |
| 5,034,413 | 7/1991 | Chan et al. . |

FOREIGN PATENT DOCUMENTS

| 0364417 | 4/1990 | European Pat. Off. . |
| 2289170 | 5/1976 | France . |
| 2293923 | 7/1976 | France . |
| WO94/06433 | 3/1994 | WIPO . |
| WO94/06432 | 3/1994 | WIPO . |

OTHER PUBLICATIONS

Caton et al, "Synthesis of Some Novel 11–Deoxyprostaglandins", *Chemistry, Biochemistry & Pharmacological Activity of Prostanoids*, 1978, pp. 27–38.

Chemical Abstracts, vol. 90, Columbus, Ohio, No. 103514h 1979.

Chemical Abstracts, vol. 90, Columbus, Ohio, No. 103508j 1979.

Bito, L. Z., "Prostaglandins and Related Compunds as Potential Ocular Therapeutic Agents," *Biological Protection with Prostaglandins*, Cohen, M. M., ed., Boca Raton, Fla., CRC Press, Inc., 1985, pp. 231–252.

Bito, L. Z., "Prostaglandins, Other Eicosanoids, and Their Derivatives as Potential Antiglaucoma Agents," *Applied Pharmacology in the Medical Treatment of Glaucomas* Drance, S. M. and Neufeld, A. H. eds., New York, Grune & Stratton, 1984, pp. 477–505.

Nilsson, et al., "$PGF_{2\alpha}$ Increases Uveoscleral Outflow," *Invest. Ophthalmol. Vis. Sci.* (suppl), 284, 1987.

Siebold, et. al., "Esterified prostaglandin shows 'potent' promise," *Prodrug* 53, 1989.

Bito, L. Z., "Prostaglandins, Old Concepts and New Perspectives," *Arch. Ophthalmol.* 105, 1036, 1987.

*Primary Examiner*—Zohreh Fay
*Attorney, Agent, or Firm*—Robert J. Baran; Martin A. Voet; Howard R. Lambert

[57] ABSTRACT

The present invention provides therapeutic agents comprising cyclopentane heptane or heptenoic acid, 2 arylalkyl or arylalkenyl and derivatives thereof, wherein the carboxylic acid of the parent compound is converted to a hydroxyl or ester group. These therapeutic agents are potent ocular hypotensives as well as having other therapeutic uses.

10 Claims, No Drawings

1

CYCLOPENTANE HEPTANOIC OR HEPTENOIC ACID, 2-ARYLALKYL OR ARYLALKENYL AND DERIVATIVES AS THERAPEUTIC AGENTS

FIELD OF THE INVENTION

The present invention relates to the use of cyclopentane heptanoic or heptenoic acid, 2-arylalkyl or arylalkenyl as therapeutic agents. In the compounds used in the method of the present invention, the carboxylic acid group of the above parent compound may be converted to a compound comprising a hydroxyl or ester group in the 1-position. These derivatives of cyclopentane heptanoic or heptenoic acid, 2-(arylalkyl or arylalkenyl) of the present invention are potent ocular hypotensives, and are particularly suitable for the management of glaucoma. Moreover, these derivatives are smooth muscle relaxants with broad application in systemic hypertensive and pulmonary diseases; smooth muscle relaxants with application in gastrointestinal disease, reproduction, fertility, incontinence, shock, etc.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M. S. *Exp. Eye Res.* 1971, 11, pp. 170–177; Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}, PGF_{1\alpha}, PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15- 9,15- and 9,11-diesters of prostaglandins, for example 11,15 -dipivaloyl $PGF_{2\alpha}$ are known to have ocular hypotensive activity. See the co-pending patent applications U.S. Ser. No. 385,645 filed 27 Jul. 1990, now U.S. Pat. No. 4,494,274; U.S. Ser. No. 584,370 which is a continuation of U.S. Ser. No. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by reference.

SUMMARY OF THE INVENTION

We have found that certain cyclopentane heptanoic or heptenoic acid, 2-arylalkyl or arylalkenyl and derivatives thereof wherein the carboxylic acid group is replaced by a non-acidic substituent have pronounced effects on smooth muscle and are potent ocular hypotensive agents. We have further found that such derivatives may be significantly more potent than their respective parent compounds and, in the case of glaucoma surprisingly, cause no or significantly lower ocular surface hyperemia than the parent compounds.

The present invention relates to methods of treating cardiovascular, pulmonary-respiratory, gastrointestinal, reproductive, allergic disease, shock and ocular hypertension which comprises administering an effective amount of a compound represented by the formula I

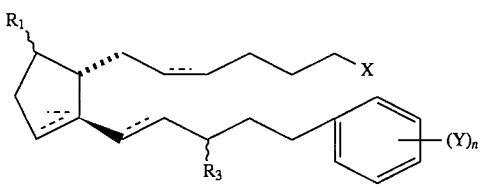

wherein the solid triangle indicates beta (β) configuration; the hatched line indicates α configuration; the wavy line indicates either an α or β configuration, the dashed bonds represent a single bond or a double bond which can be in the cis or trans configuration; X is a radical selected from the group consisting of

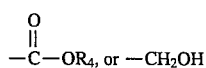

wherein $R_4$ is hydrogen or a lower alkyl radical having up to 6 carbon atoms; Y is a radical selected from the group consisting of halo, nitro, amino, thiol, hydroxy, alkyloxy and alkylcarboxy; $R_1$ is —OH, or a —O(CO)$R_6$ group and $R_3$ is —OH or an —O(CO)$R_6$ group, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring having from about 3 to about 7 carbon atoms, or an aromatic or heteroaromatic ring, e.g. a phenyl, thienyl, furanyl or pyridyl ring; or a pharmaceutically acceptable salt thereof.

More preferably the method of the present invention comprises administering a compound represented by the formula II

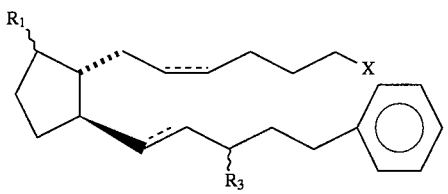

Formula II wherein the symbols and substituents are as defined above. Preferably $R_1$ and $R_3$ are —OH.

In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a compound of formula (III)

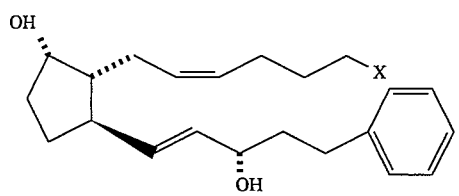

wherein the symbols and substituents are as defined above, in combination with a pharmaceutical carrier.

In a further aspect, the present invention relates to pharmaceutical compositions comprising a therapeutically effective amount of a compound of the formulae (I), (II), or (III) wherein the symbols have the above meanings, or a pharmaceutically acceptable salt thereof in admixture with a non-toxic, pharmaceutically acceptable liquid vehicle.

DETAILED DESCRIPTION OF THE INVENTION

The present invention relates to the use of cyclopentane heptanoic or heptenoic acid, 2-arylalkyl or arylalkenyl and derivatives thereof as therapeutic agents, e.g. as ocular hypotensives. These therapeutic agents are represented by compounds having the formula I,

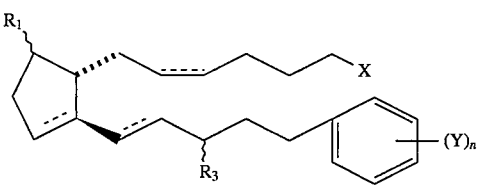

as defined above.

The preferred cyclopentane heptenoic acid, 2-(phenyl alkyl or phenylalkenyl) or derivatives thereof used in accordance with the present invention are encompassed by the following structural formula (II)

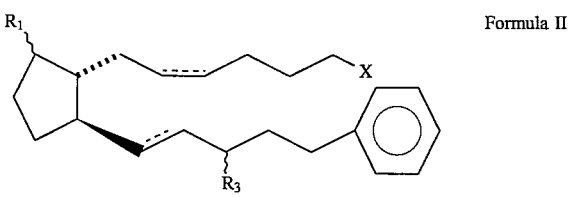

Formula II wherein the substituents and symbols are as hereinabove defined.

More preferably the compounds and derivatives thereof are represented by formula (III).

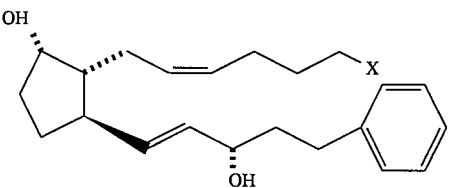

wherein the substituents and symbols are as defined above.

Most preferably, the derivatives utilized in the present invention are compounds represented by the formula (IV)

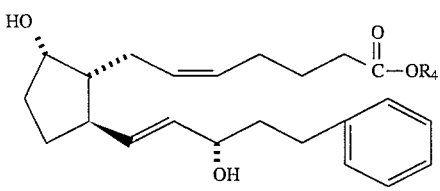

wherein the substituents and the symbols are as defined above.

In all of the above formulae the dotted lines on bonds between carbons 5 and 6 (C-5) of the α chain, between carbons 13 and 14 (C-13) of the ω chain, and between carbons 11 and 12 (C-11) of the cyclopentane ring, indicate a single or a double bond, except for the C-11 bond, which can be in the cis or trans configuration. If two solid lines are used that indicates a specific configuration for that double bond. Hatched lines at positions C-8, C-9, and C-15 indicate the α configuration. If one were to draw the β configuration, a solid triangular line would be used.

In the compounds used in accordance with the present invention, compounds having the C-8, C-9, or C-15 substituents in the α or β configuration are contemplated.

For the purpose of this invention, unless further limited, the
term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, $-(CH_2)_m R_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_7$ preferably is phenyl, and the heteroaromatic rings have oxygen, nitrogen or sulfur as a heteroatom, i.e., $R_7$ may be thienyl, furanyl, pyridyl, etc. Preferably m is 0–4.

X may be selected from the group consisting of:

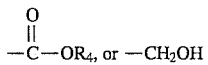

wherein $R_4$ is hydrogen or a lower alkyl radical having up to 6 carbon atoms. Preferably $R_4$ is methyl or ethyl.

Preferred representatives of the compounds within the scope of the present invention are the compounds of formula IV wherein X is —C(=O)OR_4, i.e. cyclopentane heptenoic acid, 5-cis-2-(3-αhydroxy-5-phenyl-1-trans-pentenyl)-3-hydroxy, [1α,2β,5α] and the 9- and/or 15-esters of this compound. (The numbered designations in brackets refer to the positions on the cyclopentane ring.)

The following novel compounds may be used in the pharmaceutical compositions and the methods of treatment of the present invention.

(1) cyclopentane heptenol-5-cis-2-(3-αhydroxy-5-phenyl-1 -trans-pentenyl)-3-hydroxy, [1α,2β,5α]
(2) cyclopentane heptenol-5-cis-2-(3-αhydroxy-4 -m-chlorophenoxy-1-trans-butenyl)-3-hydroxy, [1α,2β,5α]
(3) cyclopentane heptenoic acid 5-cis-2-(3-αhydroxy-5 -phenyl-1-trans-pentenyl)-3-hydroxy, [1α,2β,5α], methylester
(4) cyclopentane heptenoic acid 5-cis-2-(3-αhydroxy-5 -phenyl-1-trans-pentenyl)-3-hydroxy, [1α,2β,5α], ethylester
(5) cyclopentane heptenoic acid-5-cis-2-(3-αhydroxy-5 -phenyl-1-trans-pentenyl)-3-hydroxy, [1α,2β,5α], isopropylester A pharmaceutically acceptable salt is any salt which retains the activity of the parent compound and does not impart any deleterious undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjuster | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 ml.

The invention is further illustrated by the following non-limiting Examples.

Example 1

[3aα,4α]-3,4,7,8-Tetrahydro-2-oxo-cyclopenta[b]furan-4-carboxaldehyde (2).

To a stirred solution of oxalyl chloride (1.8 mL, 20 mmol) in dichloromethane (54 mL) at −78° C. was added dropwise dimethylsulfoxide (2.9 mL, 41 mmol). The resulting solution was maintained at −78° C. for 2 min, then a solution of [3aα,4α,5β,6aα]-hexahydro-5-benzoyloxy-4-hydroxymethyl-2-oxo-cyclopenta[b]furan (1) (3.74 g, 13.5 mmol) in dichloromethane (13 mL) was added dropwise. The resulting mixture was maintained at −78° C. for 45 min, then to the reaction was added triethyl amine (9.4 mL, 68 mmol) in one portion. The reaction was removed from the cold bath and allowed to warm to room temperature and was maintained at that temperature for 2 h. The reaction was then diluted with dichloromethane (100 mL) and washed with water (2×20 mL) and brine (1×20 mL) then was dried ($Na_2SO_4$) and concentrated in vacuo to provide the title compound 2 as a clear, slightly yellow oil (1.87 g, 12.3 mmol).

Example 2

[3aα,4α,5α]-Hexahydro-2-oxo-cyclopenta[b]furan-4-carboxaldehyde (3).

A mixture of [3aα,4α]-3,4,7,8-tetrahydro-2-oxo-cyclopenta[b]furan-4-carboxaldehyde (2) (1.72 g, 11.3 mmol) and 10% palladium on charcoal (1.20 g, 1.1 mmol) in tetrahydrofuran (55 mL) under a blanket of hydrogen was vigorously stirred for 17 h. The reaction was then filtered through a plug of celite with the aid of ethyl acetate (100 mL) and concentrated in vacuo to provide the title compound 3 as a clear, colorless oil (1.20 g, 1.13 mmol). $R_f$=0.36 in ethyl acetate-hexanes, 1:2.

Example 3

[3aα,4α,5β]-Hexahydro-2-oxo-cyclopenta[b]furan-4-carboxaldehyde (4).

A mixture of [3aα,4α,5α]-hexahydro-2-oxo-cyclopenta[b]furan-4-carboxaldehyde (3) (945 mg, 6.13 mmol) and 1,8-diazabicyclo[5.4.0]undec-7-ene (50 μL, 0.3 mmol) in tetrahydrofuran was stirred for 2 h then diluted with ethyl acetate (30 mL) and washed with water (2×10 mL) and brine (1×10 mL). The reaction was then dried ($Na_2SO_4$) and concentrated in vacuo. Column chromatography provided the title compound as a clear, colorless oil (780 mg, 5.05 mmol). $R_f$=0.36 in ethyl acetate-hexanes, 1:2.

Example 4

[3aα,4α,5β]]-Hexahydro-2-oxo-4-(5-phenyl-3-oxo-1E-pentenyl)-cyclopenta[b]furan (5).

To a solution of dimethyl(2-oxo-4-phenylbutyl)phosphonate (1.40 g, 5.46 mmol), [3 aα,4β,5α]-hexahydro-2-oxo-cyclopenta[b]furan-4-carboxaldehyde (4) (0.765 mg, 4.96 mmol) and triethylbenzyl ammonium chloride (110 mg 0.48 mmol) in dichloromethane (10 mL) at room temperature was added a 10M aqueous solution sodium hydroxide (0.55 mL, 5.5 mmol) and the resulting mixture was vigorously stirred for 40 min. The reaction was then diluted with ethyl acetate and washed with water (2×10 mL) and brine (1×10 mL) and concentrated in vacuo. Column chromatography (1:2 ethyl acetate-hexanes through silica gel) provided the title compound 5 as a clear, colorless oil (1.29 g, 4.53 mmol). $R_f$=0.42 in ethyl acetate-hexanes, 1:1.

Example 5

[3aα,4α,5β]-Hexahydro-2-oxo-4-(5-phenyl-3-hydroxy-1E-pentenyl)-cyclopenta[b]furan (6).

To a solution of [3aα,4α,5β]-hexahydro-2-oxo-4-(5-phenyl-3-oxo-1E-pentenyl)-cyclopenta[b]furan (5) (1.29 g, 4.54 mmol) and cerium trichloride heptahydrate (680 mg, 1.82 mmol) in methanol (23 mL) at −78° C. was added sodium borohydride (260 mg, 6.80 mmol). The reaction was maintained at −78° C. for 30 min, then was removed from the cold bath and allowed to warm to room temperature over 2 h. The reaction was the diluted with ethyl acetate and washed with water (2×10 mL) and brine (1×10 mL) then concentrated in vacuo. Column chromatography (1:1 ethyl acetate-hexanes through silica gel) provided the title compounds as a clear, colorless oil. [3aα,4α,5β] -hexahydro-2-oxo-4-(5-phenyl-3α-hydroxy-1 E-pentenyl)cyclopenta[b]furan (6a) (541 mg, 1.90 mmol). Rf=0.36 in ethyl acetate-hexanes. [3aα,4α,5β]-hexahydro-2-oxo-4 -(5-phenyl-3β-hydroxy-1E-pentenyl)-cyclopenta[b]furan (6b) (499 mg, 1.74 mmol). $R_f$=0.30 in ethyl acetate-hexanes, 1:2.

Example 6

[3aα,4α,5β]-Hexahydro-2-oxo-4-(5-phenyl-3α-t-butyldimethylsiloxy-lE-pentenyl)cyclopenta[b]furan (7a)

To a solution [3aα,4β,5α]-hexahydro-2-oxo-4-(5-phenyl-3α-hydroxy-1E-pentenyl)-cyclopenta[b]furan (6a) (540 mg, 1.80 mmol) and 2,6 lutidine (0.43 mL, 3.8 mmol) in N,N-dimethyl formamide (9.4 mL) at room temperature was added t-butyldimethylsilyl chloride in one portion (0.43 g, 2.8 mmol). The reaction was maintained at room temperature for 12.4 h then was the diluted with ethyl acetate (40 mL), washed with water (2×10 mL) and brine (1×10 mL), dried ($Na_2SO_4$) then concentrated in vacuo. Column chromatography (1:4 ethyl acetate-hexanes through silica gel)

provided the title compound 7a as a clear, colorless oil. (643 mg, 1.60 mmol) (Rf=0.4 in 1:4 ethyl acetate in hexanes).

Examples 7

[3aα,4β,5β]-Hexahydro-2-oxo-4-(5-phenyl-3β -t-butyldimethylsiloxy-1E-pentenyl)cyclopenta[b]furan (7b).

Using the general procedure described above in Example 6 [3aα,4α,5β]-hexahydro-2-oxo-4-(5-phenyl-3α-hydroxy-1 E-pentenyl)-cyclopenta[b]furan (6b) (493 mg, 1.72 mmol) was converted to the title compound 7b (520 mg, 1.30 mmol) Rf=0.4 in 1:4 ethyl acetate in hexanes.

Examples 8

[3aα,4α,5β]-Hexahydro-2-hydroxy-4-(5-phenyl-3α -t-butyldimethylsiloxy-1E-pentenyl)cyclopenta[b]furan (8a).

To a solution [3aα,4α,5β]-hexahydro-2-oxo-4-(5-phenyl-3α-t-butyldimethylsiloxy-1E-pentenyl)-cyclopenta[b]furan (7a) (593 mg, 1.48 mmol) in dichloromethane (7.4 mL) at −78° C. was added a 1.0M stock solution of diisobutyl aluminum hydride in dichloromethane (2.2 mL, 2.2 mmol). The reaction was maintained at −78° C. for 16 h, then was quenched into a rapidly stirring solution of water in dichloromethane. After 2 h, the reaction was filtered and concentrated in vacuo to provide the title compound as a clear, slightly yellow oil (590 mg, 1.46 mmol).

Examples 9

[3aα,4α,5β]]-Hexahydro-2-hydroxy-4-(5-phenyl-3β -t-butyldimethylsiloxy-1E -pentenyl)cyclopenta[b]furan (8b).

Using the genera procedure described above in Example 8 [3aα,4α,5β]]-hexahydro-2-oxo-4-(5-phenyl-3β -t-butyldimethylsiloxy-1E-pentenyl)-cyclopenta[b]furan (8a) (501 mg, 1.25 mmol) was converted to the title compound 8b (455 mg, 1.13 mmol).

Examples 10

[1aα,2aβ,5ab]7-[5-hydroxy-2-(-5-phenyl-3α -t-butyldimethylsiloxy-1E -pentenyl)-2-cyclopentenyl]-5Z-heptenoic acid (9a).

To a stirred solution of the (4-carboxybutyl)triphenylphosphonium bromide (1.37 g, 3.10 mmol) in dimethyl sulfoxide (15.5 mL) at room temperature was added a 1.0M stock solution of sodium bis(trimethylsilyl)amide in tetrahydrofuran (6.2 mL, 6.2 mmol) dropwise over about 5 min. The reaction mixture turned slightly yellow then cherry red during this addition. After the addition was complete, the reaction was maintained at room temperature for an additional 35 min, then a solution of [3aα,4α,5β]-hexahydro-2-hydroxy-4-(5 -phenyl-3α-t-butyldimethylsiloxy-1E-pentenyl)-cyclopenta[b]furan (8a) (216 mg, 0.536 mmol) in tetrahydrofuran (2 mL) was added by canula. After 2.5 h, the reaction was poured into 35 mL of water and neutralized to pH 7 with concentrated HCl. The reaction was then extracted into ethyl acetate (3×10 mL). The aqueous portion was then acidified to pH 3 with concentrated HCl then extracted into additional ethyl acetate (3×10 mL). The combined organic layers were then washed with brine (3×5 mL), dried over anhydrous $MgSO_4$, filtered and concentrated in vacuo to provide the title compound 9a as a yellow oil (208 mg, 0.427 mmol). $R_f$=0.36 in ethyl acetate-hexanes, 1:2.

Examples 11

[1aα,2aβ,5ab]7-[5-hydroxy-2-(-5-phenyl-3β -t-butyldimethylsiloxy-1E-pentenyl)-2-cyclopentenyl]-5Z -heptenoic acid (9b).

Using the general procedure described above in Example 10 [3aα,4α,5β]]-hexahydro-2-hydroxy-4-(5-phenyl-3β -t-butyldimethylsiloxy-1E-pentenyl)-cyclopenta[b]furan (8b) (425 mg, 1.05 mmol) was converted to the title compound 9b (237 mg, 0.490 mmol). (Rf=0.3 in 30% ethyl acetate in hexanes). $R_f$=0.36 in ethyl acetate-hexanes, 1:2.

Examples 12

[1aα,2aβ,5ab]7-[5-Hydroxy-2-(-5-phenyl-3α -hydroxy-1E-pentenyl)-2-cyclopentenyl]-5Z -heptenoic acid (10a).

To a solution of [1aα,2aβ,5aβ]7-[5-hydroxy-2-(-5-phenyl-3α-t-butyldimethylsiloxy-1E-pentenyl)-2-cyclopentenyl]-5Z-heptenoic acid (9a). (109 mg, 0.223 mmol) in anhydrous tetrahydrofuran (2.2 mL) at room temperature was added dropwise a 1.0M stock solution of tetrabutylammonium fluoride in tetrahydrofuran (0.34 mL, 0.34 mmol) over several seconds. The reaction was maintained at room temperature for 4 h, then was transferred into a separatory funnel with the aid of ethyl acetate (20 mL) and was washed with water (2×5 mL) and brine (1×10 mL). The organic portion was then concentrated in vacuo to a slightly yellow oil. Column chromatography (1:1 ethyl acetate in hexanes through silica gel) provide the title compound 10a. as a clear, colorless oil (42.1 mg, 0.113 mmol). Rf=0.18 in ethyl acetate in hexanes, 1:1.

Examples 13

[1aα,2aβ,5ab]7-[5-Hydroxy-2-(-5-phenyl-3β -hydroxy-1E -pentenyl)-2-cyclopentenyl]-5Z -heptenoic acid (10b).

Using the general procedure described above in Example 12 [1aα,2aβ,5ab]7-[5-hydroxy-2-(-5-phenyl-3β -t-butyldimethylsiloxy- 1E-pentenyl)-2-cyclopentenyl]-5Z-heptenoic acid (9b ) (89.0 mg, 0.182 mmol) was converted to the title compound 10b (22.7 mg, 0.0744 mmol).

Examples 14

[1aα,2aβ,5ab]Methyl 7-[5-hydroxy-2-(-5-phenyl-3α-hydroxy-1E-pentenyl)-2-cyclopentenyl]-5Z-heptenoic acid (11a).

To a solution of [1aα,2aβ,5ab]7-[5-hydroxy-2-(-5-phenyl-3α-hydroxy-1 E-pentenyl)-2-cyclopentenyl]-5Z-heptenoic acid (10a). (19.7 mg, 0.0529 mmol) in methanol (5 mL) at room temperature was added dropwise a stock solution of diazomethane in ether until the yellow color was maintained. The reaction was then quenched by addition of a drop of glacial acetic acid and concentrated in vacuo provide the title compound 11a as a clear, colorless oil (18.2 mg, 0.0471 mmol). Rf=0.18 in ethyl acetate in hexanes, 1:1. Partial $^1$H NMR ($CDCl_3$) δ7.16–7.24 (m, 5H), 5.50 (m, 2H), 5.33 (m, 2H), 5.13 (m, 1H), 4.08 (m, 1H), 3.63 (s, 3H), 2.68 (m, 2H), 2.35 (m, 1H), 2.26 (t, J=2.2 Hz, 2H), 2.2–1.3 (m, 13H).

Examples 15

[1aα,2aβ,5ab]Methyl 7-[5-hydroxy-2-(-5-phenyl-3β-hydroxy-1E-pentenyl)-2-cyclopentenyl]-5Z -heptenoic acid (11b).

Using the general procedure described above in Example 14 [1aα,2aβ,5ab]7-[5-hydroxy-2-(-5-phenyl-3β-hydroxy-1 E-pentenyl)-2-cyclopentenyl]-5Z-heptenoic acid (10b). (12.1 mg, 0.0324 mmol) was converted to the title compound 11b (12.2 mg, 0.0315 mmol). $R_f$=0.2 in ethyl acetate-hexanes, 1:1. Partial $^1$H NMR ($CDCl_3$) δ7.16–7.25 (m, 5H), 5.53 (dd, J=2.0, 14.9 Hz, 1H), 5.44 (dd, J=2.6, 14.9 Hz, 1H), 5.33 (m, 2H), 5.16 (m, 1H), 4.07 (m, 1H), 3.63 (s, 3H), 2.68 (m, 2H), 2.35 (m, 1H), 2.26 (t, J=2.4 Hz, 2H), 2.2–1.3 (m, 13H).

The above reactions are outlined in the following reaction scheme:

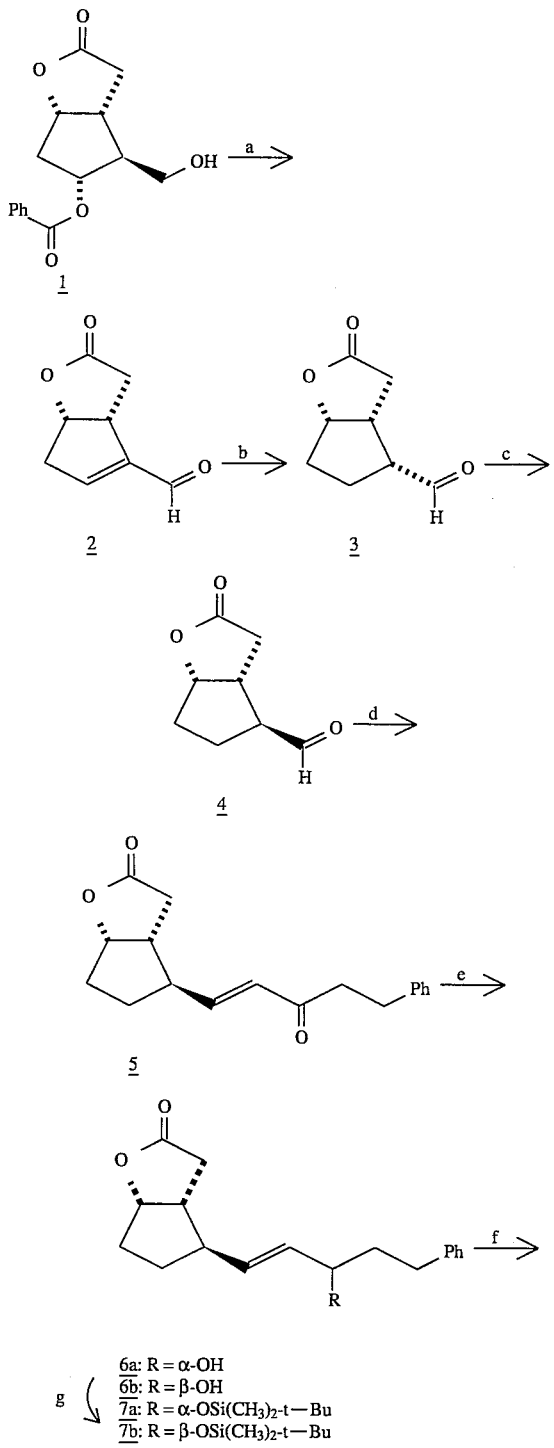

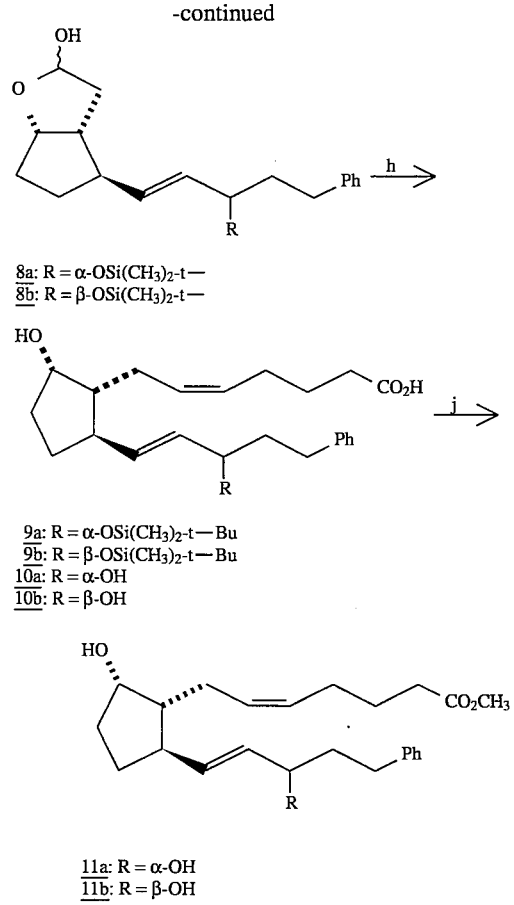

In the reaction scheme, the regents and reaction steps of the reactions described in Examples 1 through 15 are as follows:

Reagents: (a) ClCOCOl, DMSO, $CH_2Cl_2$, then $Et_3N$; (b) $H_2$, Pd(C), THF; (c) DBU, THF; (d)$(CH_3O)_2POCH_2COCH_2CH_2Ph$, NaOH(aq), $Et_3NBnCl$, $CH_2Cl_2$ (e) $NaBH_4$, $CeCl_3$, MeOH; (f) t-Bu$(CH_3)_2$SiCl, 2,6-lutidine, DMF; (g) DiBAL, $CH_2Cl_2$; (h) Br[$Ph_3P(CH_2)_5COOH$], $NaN(Si(CH_3)_3)_2$, THF, DMSO; (i) $Bu_4NF$, THF.; (j) $CH_2N_2$, MeOH.

Example 16

Testing of the Activity of Certain of the Compounds of Examples 1 through 15.

TABLE 1

Effects of 7-[2-(3-hydroxy-5-phenyl-1E-pentenyl)-5-hydroxycyclopentyl]-5Z-heptenoic acids on beagle dog intraocular pressure. Values are mean net changes in mm Hg intraocular pressure.

| Compound | Dose | maximum change |
|---|---|---|
| 11a | 0.1% | −4.0** |
| 11b | 0.1% | −1.9** | n = 6–12:
**p < 0.01 compared to baseline.

Note the compounds tested were prodrugs of the acid, i.e. the 1-methyl ester. Other prodrugs which would be expected to have activity include other lower alkyl esters as well as the 1-alcohol derivative of the carboxylic acid.

I claim:

1. A method of treating ocular hypertension which comprises applying to the eye an amount sufficient to treat ocular hypertension of a compound of formula (I)

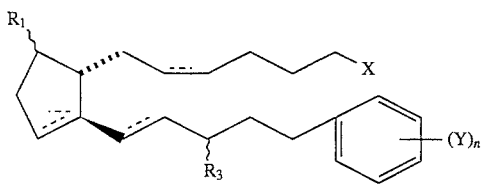

wherein the solid triangle indicates (β) configuration; the hatched line indicates α configuration; the wavy line indicates either an α or β configuration; the dashed bonds represent a single bond or a double bond which can be in the cis or trans configuration; X is a radical selected from the group consisting of

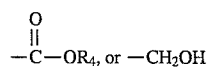

wherein $R_4$ is hydrogen or is a lower alkyl radical having up to 6 carbon atoms; Y is a radical selected from the group consisting of halo, nitro, amino, thiol, hydroxy, alkyloxy and alkylcarboxy; $R_1$ is —OH, or a —O(CO)$R_6$ group and $R_3$ is —OH or an —O(CO)$R_6$ group, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring having from about 3 to about 7 carbon atoms, or an aromatic ring; or a pharmaceutically acceptable salt thereof.

2. The method of claim 1 wherein said compound is of the formula (II)

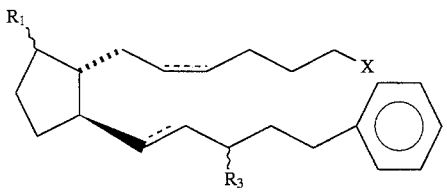

wherein the symbols and substituents are as defined in claim 1.

3. The method of claim 1 wherein said compound is of the formula (III)

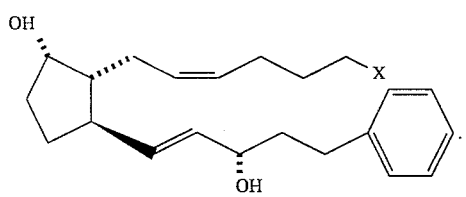

4. The method of claim 3 wherein said compound is of the formula (IV)

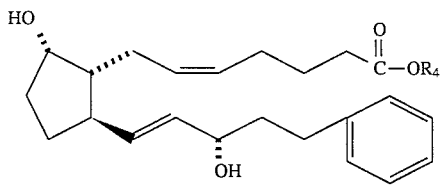

wherein the symbols and substituents are as defined as in claim 1.

5. The method of claim 4 wherein $R_4$ is methyl.

6. An ophthalmic solution comprising a therapeutically effective amount of a compound of formula (I)

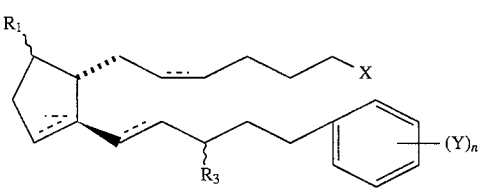

wherein the solid triangle indicates beta (β) configuration; the hatched line indicates α configuration; the wavy line indicates either an α or β configuration; the dashed bonds represent a single bond or a double bond which can be in the cis or trans configuration; X is a radical selected from the group consisting of

wherein $R_4$ is hydrogen or is a lower alkyl radical having up to 6 carbon atoms; Y is a radical selected from the group consisting of halo, nitro, amino, thiol, hydroxy, alkyloxy and alkylcarboxy; $R_1$ is =O, —OH, or an —O(CO)$R_6$ group, and $R_3$ is —OH or an —O(CO)$R_6$ group, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring having from about 3 to about 7 carbon atoms, or an aromatic ring; or a pharmaceutically acceptable salt thereof.

7. The ophthalmic solution of claim 6 comprising at least one ingredient selected from the group of an ophthalmically acceptable preservative, buffer system, antioxidant and chelating agent.

8. The ophthalmic solution of claim 7 wherein said compound is of the formula (II)

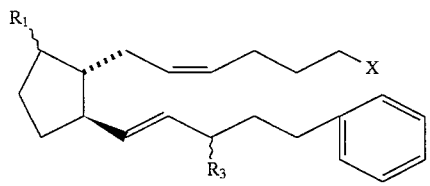

wherein the symbols and substituents are as defined in claim 6.

9. The ophthalmic solution of claim 8 wherein said compound is of the formula (III)

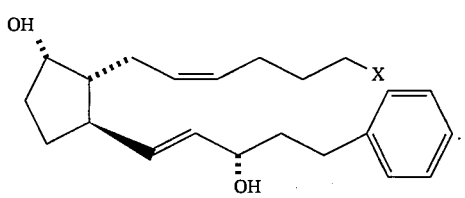
10. A pharmaceutical product, comprising
a container adapted to dispense its contents in metered form; and
an ophthalmic solution therein, as defined in claim 9.
* * * * *

UNITED STATES PATENT AND TRADEMARK OFFICE
CERTIFICATE OF CORRECTION

PATENT NO. : 5,486,540
DATED : January 23, 1996
INVENTOR(S) : Steven W. Andrews

It is certified that error appears in the above-indentified patent and that said Letters Patent is hereby corrected as shown below:

In the Abstract, line 2; delete "heptane" and insert in place thereof --heptanoic--

Column 3, line 15; delete the formula and insert in place thereof

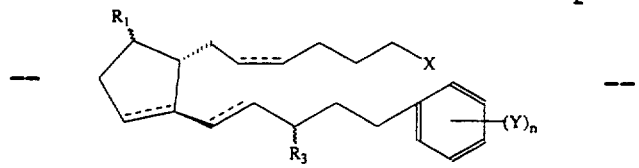

Column 6, line 9; before "undesirable" insert --or--

Column 7, line 41; delete "hydroxym" and insert in place thereof --hydroxy--

Column 7, line 42; delete "ethyl" and insert in place thereof --methyl--

Column 10, line 24; delete "10a." and insert in place thereof --10a-- ns Patent and Trademark Office

CERTIFICATE OF CORRECTION

PATENT NO. : 5,486,540
DATED : Jan. 23, 1996
INVENTOR(S) : Steven W. Andrews

It is certified that error appears in the above-indentified patent and that said Letters Patent is hereby corrected as shown below:

Columns 11 and 12; delete formulas "a - h" and insert in place thereof

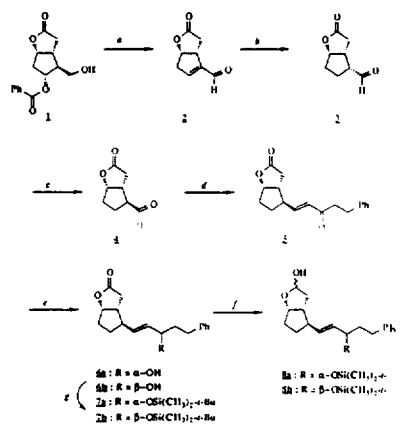

Signed and Sealed this

Second Day of July, 1996

Attest:

BRUCE LEHMAN

Attesting Officer          Commissioner of Patents and Trademarks